United States Patent [19]

Nietupski

[11] Patent Number: 5,336,680
[45] Date of Patent: Aug. 9, 1994

[54] SMOKING SUPPRESSANT AND METHOD OF APPLICATION THEREOF

[76] Inventor: Ronald S. Nietupski, 16500 Spaniel Dr., Lockport, Ill. 60441

[21] Appl. No.: 63,258

[22] Filed: May 18, 1993

[51] Int. Cl.$^5$ .............................................. A61K 31/44
[52] U.S. Cl. ..................................................... 514/354
[58] Field of Search .......................................... 514/354

[56] References Cited

U.S. PATENT DOCUMENTS 4,255,439  3/1981  Cooper ................................. 424/273
4,521,427  6/1985  Nietupski ........................... 514/354

OTHER PUBLICATIONS

Probability and Statistics for Engineers and Scientists, R. E. Walpole & R. H. Myers, the MacMillan Company, pp. 168–173 & 460 (1972).

*Primary Examiner*—José G. Dees
*Assistant Examiner*—Samuel Barts
*Attorney, Agent, or Firm*—Todd S. Parkhurst; Stuart I. Graff; Lynn E. Rzonca

[57] ABSTRACT

A method for suppressing the desire to smoke is disclosed. The method comprises inhaling an effective amount of a volatile smoking suppressant composition comprising an effective amount of 2-acetylpyridine.

8 Claims, 1 Drawing Sheet

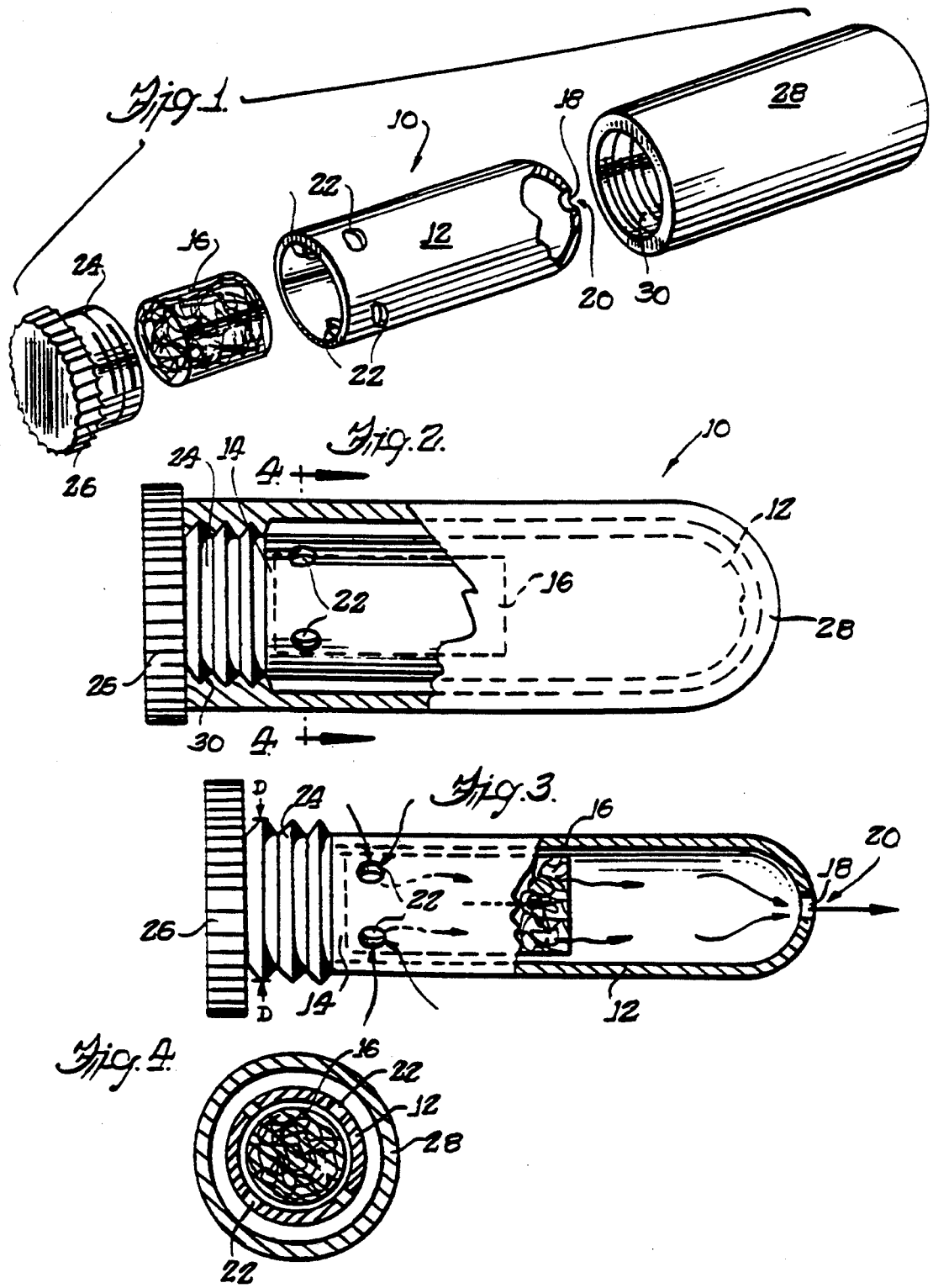

SMOKING SUPPRESSANT AND METHOD OF APPLICATION THEREOF

BACKGROUND OF THE INVENTION

This invention relates to a novel means of suppressing the desire to smoke tobacco or tobacco related products. The invention includes a novel suppressant, a method of applying the smoking suppressant, and an inhaler for the suppressant. An appetite-suppressant inhaler is disclosed in my U.S. Pat. No. 4,521,427.

Aids to stop smoking are well known. Most of these are taken orally, but some utilize a "transdermal" delivery system, i.e., the "nicotine patch," or an attempt is made to modify behavior through either hypnosis or group therapy. Some aids are temporary, ineffective under certain conditions, and can be harmful to the user.

SUMMARY OF THE INVENTION

It is a general object of this invention to provide a smoking suppressant that is effective yet extremely easy to use.

A specific object is to provide such a smoking suppressant which can be inhaled.

Another object is to provide the smoking suppressant in varying degrees of odor intensity so as to effect specific levels or types of behavior modification or maintenance.

A related object is to provide an inhaler device for presenting or offering the smoking suppressant.

Briefly, and in accordance with the foregoing objects, a novel method for suppressing the desire to smoke of an individual is provided. This method comprises inhaling an effective and specific amount of a volatile smoking suppressant, so as to stimulate the olfactory bulb which has a direct connection to the ventromedial nucleus of the hypothalamus. This is the area within the hypothalamus that is known as the "satiety center," the cerebral apparatus that triggers the sensation of satisfaction or gratification.

Fenaroli's *Handbook of Flavor Ingredients* specifies that 2-Acetylpyridine's "organoleptic characteristic" is that of a tobacco-like aroma. The direct connection between the olfactory bulb and the ventromedial nucleus of the hypothalamus is the medium by which that tobacco-like aroma, or "organoleptic sense impression" is transmitted from the olfactory receptor to that part of the satiety center that gratifies and/or satisfies the desire to smoke. The "organoleptic characteristic" elicits the "organoleptic effect" or response. In other words, it tricks the brain into thinking it has had enough, or more than enough of smoking, thereby suppressing or controlling the desire to smoke.

BRIEF DESCRIPTION OF THE DRAWING

Other objects and advantages of the invention will become apparent upon reading the following detailed description and upon reference to the drawings, in which:

FIG. 1 is an exploded view of the smoking suppressant inhaler;

FIG. 2 is a side or top view, in partial section, of the cylindrical inhaler;

FIG. 3 is a side or top view, in partial section, of a suppressant-substance-containing tube; and FIG. 4 is a sectional view taken substantially in the plane of line 4—4 in FIG. 2.

Throughout the drawings, like reference numerals refer to like parts.

DETAILED DESCRIPTION OF THE ILLUSTRATED EMBODIMENT

A smoking-suppressant inhaler 10 is shown in FIG. 1. The inhaler or device 10 comprises an elongated tube 12 having an end closure 14. The tube 12 surrounds a support means 16 into which the smoking suppressant described below is impregnated. The support means 16 can be paraffin, gauze or the like. The tube 12 includes a through outlet aperture 18 adjacent an inhalation zone or region 20 set apart from the support means 16. A plurality of (preferably four) circumferentially-spaced through inlet apertures 22 are proximate to the end closure 14. Those apertures 18, 22 permit an individual user to draw air into the tube 12 via the inlet apertures 22, across the support means 16 and out the outlet aperture 18 (FIG. 3). The volatile suppressant is transferred from the support means 16 and into the air. Air being drawn across the support means 16 picks up suppressant vapors and transfers these vapors to the inhalation zone or region 20, whereby the individual can inhale the vapors for suppressing smoking or controlling the desire to smoke.

The tube 12 preferably further includes circumferential screw threads 24 formed integral with the end closure 14 and in distal relation to the outlet orifice 18, and a knurled end 26, preferably circular in cross section. The end 26 has a diameter which is greater than that of the tube 12, and greater than the outer diameter D (FIG. 3) of the threads 24. It can be appreciated that the threads 24 and end 26 permit the tube 12 to be screwed into a second tube or closure 28 open only at a threaded end. So closing the inhaler 10 curtails undesired volatilization of the smoking suppressant from the support means 16. The second tube 28 preferably includes integral threads 30 (FIGS. 1 and 2) which mesh with the threads 24 so as to accomplish this purpose.

THE SMOKING SUPPRESSANT

It is well known that moisture is a vehicle which delivers molecular odor perception to olfactory receptors of an individual; those receptors are located at the very top of the nasal cavity near the inner end of a persons throat. I have found, and documented in my U.S. Pat. No. 4,521,427, that such receptors (when stimulated by a 10 ml. concentration of 2-Acetylpyridine per 1 liter of Propylene Glycol) can trigger appetite suppression and curb one's immediate desire to eat. During my work, I found that a dry nose and palate/tongue are incapable of detecting substantial amounts of smell or taste. Consequently, it appears that this 10 ml/liter concentration of 2-Acetylpyridine slightly and harmlessly dry the nose and palate/tongue for a short period of time and act as an appetite suppressant when it is inhaled. As a result, significant weight loss and good control of those losses were experienced.

It is generally known that smokers have a diminished ability to smell. It is for this reason smokers usually gain weight after quitting smoking—their olfactory sense or ability to smell increases because the olfactory receptors rejuvenate. In an attempt to effectively stimulate a smoker's diminished olfactory reception, I conducted clinical and practical trials utilizing an elevated 12 ml. to 20 ml. concentration of 2-Acetylpyridine per 1 liter of Propylene Glycol. I have found that smokers within this group either quit smoking, or they reduce and/or control their smoking habit. The higher the intensity, the greater the degree of success in quitting, reducing and/or controlling the habit. Further, I found that the users either lost weight or gained minimal weight during the process. These trials were prompted by the discovery that smokers were relatively unaffected, by a 10 ml. concentration of 2-Acetylpyridine per 1 liter of Propylene Glycol, during the conduct of the weight loss trials. Conversely, I found that concentrations above 10 ml. of 2-Acetylpyridine per 1 liter of Propylene Glycol were not tolerated well by non-smokers and had a negative impact on weight control. The results of these trials are presented below in Table I.

TABLE I

| USE OF ELEVATED CONCENTRATIONS OF 2-ACETYLPYRIDINE TO SUPPRESS SMOKING | | | | | | | |
|---|---|---|---|---|---|---|---|
| SUBJECT NO. | HABIT USAGE (1) | CONCEN- TRATION (2) | USAGE METHOD (3) | DURATION ON 2-A (mos.) | HABIT STATUS (4) | DEGREE OBESITY (lbs.) | WEIGHT STATUS (lbs.) | CURRENT USE 2-A (5) |
| 1. | O | B | S | 11 | O | 100 | −68 | M |
| 2. | O | A | H,P | 10 | O | 10 | 0 | N |
| 3. | U | A | S | 10 | C | 50 | −30 | M |
| 4. | O | C | P | 10 | O | 10 | −5 | B |
| 5. | O | C | S | 6 | O | 50 | −45 | B |
| 6. | O | B | S | 2 | C | 20 | −5 | B |
| 7. | O | B | S | 4 | O | 0 | 0 | N |
| 8. | O | B | S | 6 | R | 10 | 0 | B |

(1) O = over one pack per day
U = under one pack per day
(2) A = 12 ml. of 2-Acetylpyridine per 1 liter Propylene Glycol
B = 16 ml. of 2-Acetylpyridine per 1 liter Propylene Glycol
C = 20 ml. of 2-Acetylpyridine per 1 liter Propylene Glycol
(3) S = stand alone
P = with transdermal patch
H = with hypnosis
O = other
(4) O = off cigarettes
C = cut down on cigarettes
R = returned to original habit
(5) A = 12 ml. of 2-Acetylpyridine per 1 liter Propylene Glycol
B = 16 ml. of 2-Acetylpyridine per 1 liter Propylene Glycol
C = 20 ml. of 2-Acetylpyridine per 1 liter Propylene Glycol
M = 10 ml. of 2-Acetylpyridine per 1 liter Propylene Glycol
N = not using 2-Acetylpyridine
NOTE: In 1987, 50 subjects in Paraguay, South America were tested, using a 10 ml/l concentration for weight loss purposes. The majority of the subjects smoked and complained that the product suppressed their desire to smoke and for that reason discontinued its use.

Applications for various concentrations of 2-Acetylpyridine per liter of Propylene Glycol and resultant smoke suppression effects are presented below in Table II:

TABLE II

| Concentration of 2-Acetylpyridine Per Liter of Propylene Glycol | Application (Effect) |
|---|---|
| 20 ml | quit/reduce smoking |
| 16 ml | reduce/control smoking |
| 12 ml | maintenance/reinforcement |

In addition, I have discovered that repeated inhalation of this odor appears to have a behavior modifying, conditioning effect. For example, after repeated use of my invention, simply deciding to reach for or touch the inhaler can trigger the smoke suppression effect. Thereafter, the maintenance inhaler can be used on an as needed basis to reinforce the desired effect/behavior modification. In essence, once the desired effect/behavior modification takes place, very little or no external stimulus is required to maintain that effect/behavior modification.

USE OF DEVICE

Mixing of the smoking suppressant with air can be achieved in a variety of ways. For example, mixing can be achieved by placing the appetite suppressant in an inhaler 10 enclosure of the sort described above, which is supplied with an opening which restricts the rate at which vaporized smoking suppressant escapes from the enclosure. The rate can also be restricted by a porous or non-porous, but vapor-permeable, membrane.

It is currently standard procedure to match odor intensity to 1-butanol. This procedure is outlined in ASTM E 544. The smoking suppressant presented in Tables I and II was tested in accordance with ASTM E 544. I have found that odor intensities which match, preferably, 10–500 ppm (volume/volume) of 1-butanol are useful for suppressing appetite and smoking in humans. Odor intensities less than those matching 10 ppm per 1-butanol are generally too weak to be perceived, except for very sensitive individuals. Odor intensities matching more than 500 ppm of 1-butanol are quite strong, and generally appear to be needed by individuals who are rather insensitive to a particular odorant. While both the appetite and smoking suppressant concentrations lie within the 10–500 ppm of 1-butanol range, I have found that concentrations below the 10 ml/1 level are effective on non-smokers to suppress appetite, but become relatively ineffective above the 10 ml/1 level. Conversely, concentrations above the 10 ml/1 level become effective for smokers to suppress smoking, while concentrations below 10 ml/1 are relatively ineffective. Then as smokers quit or cut down on cigarettes, and their ability to smell increases, the odorant/suppressant becomes increasingly effective and can be reduced in concentration to produce a desired effect.

Odor intensity of a suppressant is affected by the solvent into which the suppressant is diluted. It is desirable to use a solvent which has substantially no odor of its own. In addition, it is desirable to use a solvent which does not modify the odor of the suppressant, and which is not toxic or irritating to skin and mucous membranes. It is also desirable that the solvent be chemically unreactive with the suppressant. Propylene glycol was used as the solvent because it meets these prerequisites, and also because it dissolves both water-and-oil-soluble suppressants. Other solvents or diluents may be effective, as well.

The suppressant can be presented to the user or consumer by the handy inhaler 10. During use, outlet aperture 18 is positioned proximate to the nostrils of an individual, and the individual inhales. This causes air to be drawn into the inlet apertures 22, across the support means 16 and out the outlet aperture 18. This passage of air across the support means 16 causes the suppressant to vaporize and to be transported from the support means 16 to the inhalation zone or region 20. From the region 20 the vapors are drawn by the individual user via the nostrils to the olfactory receptors. The quantity of suppressant thus inhaled by an individual is subjective and generally varies from one individual to another.

The smoking suppressant can be used without the imposition of other smoking aids or can be used as reinforcement or as a complement to these techniques. In either case, the user benefits from the ability to choose a specific intensity to effect or maintain a desired result.

The odorant/suppressant and solvent tested are FDA-approved for inhalation in the concentrations disclosed. The odorant/suppressant and solvent were selected from the FDA-approved GRAS list.

What has been described here is a novel smoking suppressant. While the suppressant of the present invention has been described with reference to a preferred device for application thereof, the invention is not limited to such an applicator. On the contrary, alternatives, changes or modifications may become apparent to those skilled in the art upon reading the foregoing description. Accordingly, such alternatives, changes or modifications are to be considered as forming a part of the invention insofar as they fall within the spirit and scope of the appended claims.

I claim:

1. A method of smoking suppression which comprises administration by inhalation to a person in need thereof, a volatile smoking suppressant composition comprising an effective amount 2-acetylpyridine.

2. The method of claim 1 including administering said 2-acetylpyridine in a solvent of propylene glycol or a diluent of similar characteristics.

3. The method of claim 2 wherein smoking suppressant includes from about 12 ml to about 20 ml of 2-acetylpyridine per liter of propylene glycol.

4. The method of claim 3 wherein said suppressant has an odor intensity range substantially matching from about 10 to about 500 ppm (volume/volume) of 1-butanol/air.

5. A smoking suppressant for humans comprising as a suppressant 2-acetylpyridine diluted in an effective amount of propylene glycol solvent.

6. A smoking suppressant according to claim 5 wherein said 2-acetylpyridine glycol are contained in an inhaler device.

7. A smoking suppressant according to claim 5 comprising from about 12 ml to about 20 ml of 2-acetylpyridine per liter of propylene glycol.

8. A smoking suppressant according to claim 5 wherein said suppressant has an odor intensity range substantially matching from about 10 to about 500 ppm (volume/volume) of 1-butanol/air.

* * * * *